United States Patent [19]

Pusinelli

[11] Patent Number: 5,386,734
[45] Date of Patent: Feb. 7, 1995

[54] CENTRIFUGE SYSTEM FOR THE SEPARATION OF BLOOD INTO ITS COMPONENTS

[75] Inventor: Thomas Pusinelli, Altenstadt-Waldsiedlung, Germany

[73] Assignee: Fresenius AG, Bad Homburg, Germany

[21] Appl. No.: 109,676

[22] Filed: Aug. 20, 1993

[30] Foreign Application Priority Data

Aug. 21, 1992 [DE] Germany .................. 4227695

[51] Int. Cl.6 .................................. G01N 33/49
[52] U.S. Cl. .................. 73/863.21; 210/782; 494/37; 604/4; 604/6
[58] Field of Search ............ 73/863.21; 210/781, 210/782; 494/35, 37; 604/4, 5, 6; 422/44, 72

[56] References Cited

U.S. PATENT DOCUMENTS

| | | | |
|---|---|---|---|
| 3,655,123 | 4/1972 | Judson et al. | 422/44 |
| 4,086,924 | 5/1978 | Latham, Jr. | 128/214 R |
| 4,113,173 | 9/1978 | Lolachi | 233/25 |
| 4,151,844 | 5/1979 | Cullis et al. | |
| 4,185,629 | 1/1980 | Cullis et al. | 494/37 |
| 4,187,979 | 2/1980 | Cullis et al. | 494/37 |
| 4,531,932 | 7/1985 | Luppi et al. | 604/6 |
| 4,557,719 | 12/1985 | Neumann et al. | 494/37 |
| 4,675,117 | 6/1987 | Neumann et al. | 210/789 |
| 4,834,890 | 5/1989 | Brown et al. | 210/782 |
| 5,112,298 | 5/1992 | Prince et al. | 604/4 |
| 5,135,667 | 8/1992 | Schoendorfer | 210/782 |
| 5,141,490 | 8/1992 | Fujii et al. | 604/4 |
| 5,171,456 | 12/1992 | Hwang et al. | 210/782 |
| 5,188,588 | 2/1993 | Schoendorfer et al. | 604/6 |
| 5,318,512 | 6/1994 | Neumann | 604/6 |

FOREIGN PATENT DOCUMENTS

| | | | |
|---|---|---|---|
| 2049465 | 2/1992 | Canada | 604/4 |
| 155684 | 9/1985 | European Pat. Off. | 494/35 |
| 450737A2 | 10/1991 | European Pat. Off. | |
| 0486480A2 | 5/1992 | European Pat. Off. | |
| 487096A1 | 5/1992 | European Pat. Off. | |
| 0530689A1 | 3/1993 | European Pat. Off. | |
| 3931471A1 | 4/1991 | Germany | |

Primary Examiner—Thomas P. Noland
Assistant Examiner—Daniel S. Larkin
Attorney, Agent, or Firm—Marshall, O'Toole, Gerstein, Murray & Borun

[57] ABSTRACT

A centrifuge for the separation of blood into its components, especially a single-needle centrifuge, in which, in a collecting cycle, erythrocytes and plasma are passed through a centrifuge separation chamber and temporarily stored in a storage container and, in a recirculation cycle, the blood components temporarily stored in the storage container are passed through the separation chamber again and then returned to the patient.

7 Claims, 3 Drawing Sheets

CENTRIFUGE SYSTEM FOR THE SEPARATION OF BLOOD INTO ITS COMPONENTS

BACKGROUND OF THE INVENTION

The invention is directed to a method of separating blood into its components via a centrifuge system. One such centrifuge system includes at least one sampling device for blood, such as a needle, an inlet line connected between the sampling device and a centrifuge, a blood pump connected to the inlet line, a discharge line connected between the centrifuge and a receiving container, a first pump connected to the discharge line, and a discharge line system connected to the sampling device for recycling the blood components. Such a centrifuge system is known, for example, from DE-OS 39 31 471 (Apr. 11, 1991).

Blood centrifuges or plasmaphoresis devices are known, for example, from DE-OS 26 12 988 or its counterpart U.S. Pat. No. 4,113,173, in which the blood is taken into extracorporeal circulation with the aid of a needle, introduced to a centrifuge without the use of a rotary mechanical seal, separated there into its components and then returned to the patient through a second needle. This separation treatment is carried out essentially continuously, whereby the blood is separated in the centrifuge essentially into three main components, namely, the erythrocyte component (red blood cells), the buffy coat floating on the erythrocyte component (cell mixture, principally comprising thrombocytes (platelets) and leukocytes (white blood cells)), and the plasma component (which lies radially the farthest inward in the centrifuge due to its relatively low specific gravity). The degree of separation of the leukocyte and thrombocyte components may be up to about 70%; that is, at least 30% of the leukocytes introduced into the centrifuge are returned to the patient. However, this two-needle method is relatively unpleasant for the patient.

There is a plasmaphoresis device in the form of a centrifuge in which the separation is carried out with only one needle. Such methods have been described, for example, in DE-OS 27 45 041 or its counterpart U.S. Pat. No. 4,086,924, U.S. Pat. No. 4,531,932 (Jul. 30, 1985), DE-OS 39 31 471, EP-A-450,737 (Oct. 9, 1991) and EP-A-487,096 (May 27, 1992). However, the single-needle method must be carried out intermittently; that is, in a first cycle step, blood must be taken from the patient and introduced to the centrifuge and, in a second cycle step, the blood components are then returned to the patient. Although this method normally takes longer than a two-needle separation, it is desirable or even necessary in case the veins are cartilaginous or hard to find.

Moreover, the thrombocyte component is still contaminated with a certain portion of the lymphocytes, and the leukocyte component is contaminated with a portion of the erythrocytes and thrombocytes, so that a higher degree of purity is desirable. In order to improve the degree of separation and degree of purity, for example, DE-OS 39 31 471 proposes recirculation of certain separated blood components with untreated blood, but this brings about only a certain degree of improvement of the separating action.

SUMMARY OF THE INVENTION

The invention is directed to a method for separating blood components in a centrifuge system in which the yield and the purity of the blood fractions to be separated is improved, especially in a single-needle centrifuge system, with as short treatment times as possible.

The invention utilizes a discharge line system having a plasma discharge line, a plasma pump connected in the plasma discharge line, a plasma branch line connected at one end to the plasma discharge line at a first branching point and connected at another end to a storage container. The invention includes an erythrocyte discharge line, an erythrocyte branch line connected at one end to the erythrocyte discharge line at a second branching point and connected to the storage container at another end.

The invention further includes a collecting line connected to the storage container at one end and connected at its other end to an inlet line at a third branching point. The inlet line is coupled to a sampling device, such as a needle, and includes a blood pump.

The collecting line includes a locking or valve system which, in a collection phase or cycle during which blood is being withdrawn by the sampling device, closes the collecting line, the plasma discharge line downstream of the first branching point and the erythrocyte discharge line downstream of the second branching point. During a recirculation phase or cycle in which blood is being returned to the patient via the sampling device, the locking system closes the plasma branch line and the erythrocyte branch line and opens the plasma discharge line, the erythrocyte discharge line, and a recycling line connected to the inlet line.

With the centrifuge according to the invention, in a first cycle step, a predetermined amount of blood is separated into two fractions, a first fraction being stored in a first container and a remaining fraction being stored in an intermediate container and, in a second cycle step, the remaining fraction is subjected to repeated separation treatment whereby a further portion of the remaining fraction is separated and then the remaining blood constituents are returned to the patient or blood source.

With blood separation in accordance with the invention, the purity of the blood components obtained is increased, and the time required for separation can be kept to a minimally small value in spite of the recirculation, since, during the recirculation phase, reinfusion occurs at the same time. As a result of this, it is possible to recover blood components even during reinfusion. In addition, since the centrifuge is operated continuously, the separation time is shortened as much as possible with the highest possible effectiveness, and the centrifuge start-up time, which is necessary for the development of a significant blood component separation limit, is eliminated.

Consequently, the advantages of the invention lie in effective separation of the blood components by repeated recirculation of the same blood in as short a time as possible.

While the separation process may be carried out with the usual two-needle arrangement, the single-needle arrangement is preferred. Insofar as the sampling device has a single needle, either the end away from the patient has a Y-shaped branch or the tubing attached to the sampling device has a Y-shaped branch.

The amount of blood removed and processed during the collection phase depends essentially on the capacity of the collecting container and the storage container, which are usually in the form of bags. In this respect, the amount of blood removed from the patient (or another blood source such as a blood bag) is predetermined.

The removed blood, which is usually treated with an anticoagulant, goes through the separation treatment in the centrifuge separation chamber, where the blood is separated into its individual components. These usually consist of 1) the erythrocyte component (which is farthest to the outside of the centrifuge due to its relatively high specific gravity), 2) the bully coat, and 3) the plasma component. The adjustment of these component limits as well as the separation are carried out according to the usual method, for example, as described in DE-OS 33 01 113 or its counterpart U.S. Pat. No. 4,557,719.

After a predetermined period, these components are withdrawn from the separation chamber or are pumped out from the separation chamber under the action of the blood pump. During the collection phase, a pump pumps the white blood cell (WBC) and platelet (PLT) components into a WBC-PLT bag, while the erythrocyte component is pumped directly into the storage container under the action of the blood pump. The plasma fraction is pumped into the same storage container with the aid of the discharge pump, which is designed as a plasma pump.

The storage container is preferably designed so that it has an inclined bottom. The plasma branch line is attached to the storage container so that it opens into the lower, inclined region of the container, while the erythrocyte (red blood cells) branch line opens into the upper region. As a result, due to the higher specific gravity of the red blood cells, the plasma and red blood cells are mixed better within the storage container.

In the collection phase, the WBC-PLT bag and the storage container are filled with a specified volume. When the predetermined volume is reached in the storage container, then, with the aid of the locking device, a change in the fluid flow is produced within the extracorporeal line system as described below.

As in all extracorporeal blood systems, this system is closed to the environment and is sterile. The system may be made of a polymeric elastic material (e.g. PVC tubes and PVC bag). Due to the elasticity of such plastic tubes, external clamps can be used as locking devices for the particular tubing sections. The clamps can be designed as individual clamps or as a tube clamp arrangement; that is, they may consist of pairs of clamps which can be switched between two states (collection phase and recycling phase) and can be operated with a single control element. The latter arrangement is preferred for cost reasons.

After the conclusion of the collection phase, the system is switched into the recirculation phase. In this case, the blood inlet line is closed upstream of the third branching point and, at the same time, the collecting line leaving the storage container is opened. The erythrocyte and plasma branch lines are closed, so that no further blood components are introduced into the storage container. The plasma discharge line is opened downstream of the first branching point and the erythrocyte discharge line is opened downstream from the second branching point, so that the red blood cells and plasma can be returned to the patient or donor under the aid of the plasma pump or blood pump. The two discharge lines open advantageously into a mixing vessel from which a recycling line goes directly to the patient.

According to another aspect of the invention, a plasma collecting line is connected to the plasma discharge line at a fourth branching point downstream from the first branching point and the locking clamp in the plasma discharge line. The plasma collecting line opens into a plasma bag. A second locking system is provided downstream of the fourth branching point and can optionally lock the plasma collecting line and the plasma discharge line. As explained above, this can consist of individual locking devices (clamp arrangement) for the plasma collecting and plasma discharge lines or can consist of a pair of clamps. The second locking system is operated independently of the first locking system.

During the second pass of the blood through the centrifuge separation system, a WBC-PLT component is again obtained. The blood subjected to the separation step for the second time is reinfused completely at the flow rate, which is predetermined by the blood pump. In order to avoid unnecessary dilution of the blood to be separated and excessive reinfusion of anticoagulant solutions, anticoagulant addition is omitted during the recirculation phase.

The separation chamber, the fluid storage containers and the needle-shaped withdrawal device may advantageously be provided as a disposable system. Such a disposable system, which is closed to the environment and is sterile, may be supplied as a pre-manufactured disposable device to be used immediately after insertion into the centrifuge drive.

The centrifuge system in accordance with the invention may additionally comprise a plasma collecting line connected between a plasma collecting bag and the plasma discharge line at a fourth branching point downstream of the first clamp and clamp means disposed downstream of the fourth branching point, the clamp means alternately opening and closing the plasma discharge line and the plasma collecting line in a predetermined time frequency.

The centrifuge system may additionally comprise a level sensor for detecting the degree to which the storage container is filled, with the level sensor switching the state of a locking means after reaching a predetermined value.

Other objects and advantages of the invention will be apparent to those skilled in the art from a review of the following detailed description, taken in conjunction with the drawings and the appended claims.

DETAILED DESCRIPTION OF A PREFERRED EMBODIMENT

Figure 1:
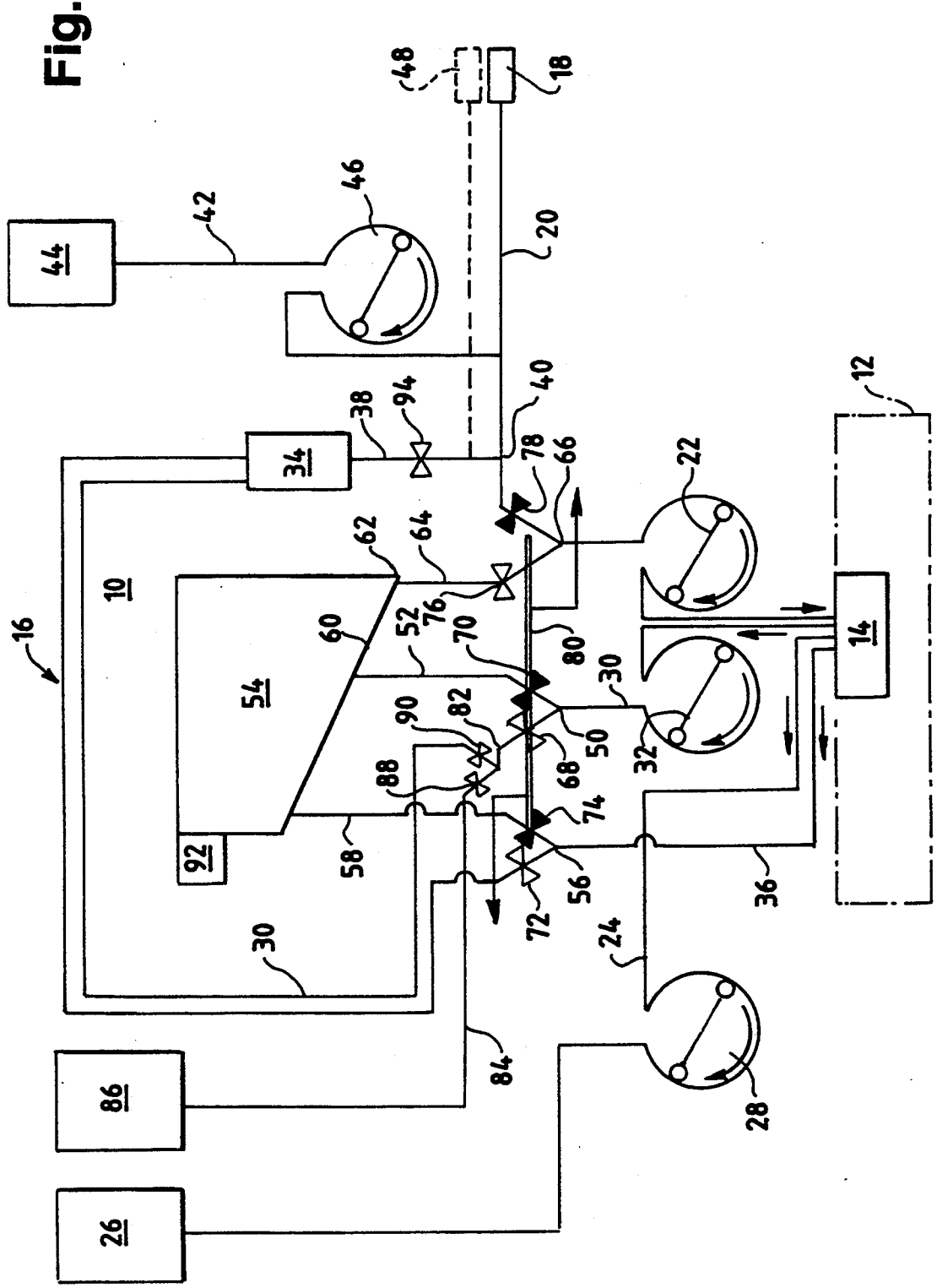
FIG. 1 is a schematic depiction of a preferred embodiment of the invention.

A preferred embodiment of a centrifuge system 10 in accordance with the invention is illustrated in FIG. 1. The centrifuge system 10 has a centrifuge drive 12, a separation chamber 14 driven by the centrifuge drive 12, and a tubing system 16 connected to the separation chamber 14.

The tubing system 16 has a needle 18 which can be inserted into a patient or a blood bag. An inlet line 20 connects the needle 18 to the separation chamber 14. A blood pump 22 in the form of a peristaltic pump is connected in the inlet line 20 to pump blood from the needle 18 to the chamber 14.

A white blood cell-platelet (WBC-PLT) line 24 is connected between the separation chamber 14 and a WBC-PLT bag 26 used as a collecting container. A WBC-PLT pump 28 is connected in the WBC-PLT line 24.

A plasma discharge line 30 is connected between the separation chamber 14 and a dropping chamber 34 used as a collecting chamber. A plasma pump 32 is disposed in the plasma discharge line 30 to pump plasma from the separation chamber 14 to the dropping chamber 34. An erythrocyte (red blood cell) discharge line 36 is connected between the separation chamber 14 and the dropping chamber 34.

A recycling line 38 is connected between the dropping chamber 34 and either to the Y-shaped needle 18, or as shown in FIG. 1, to the inlet line 20 at an entry point 40. An anticoagulant line 42 is connected to supply anticoagulant to the inlet line 20 from an anticoagulant container 44 via an anticoagulant pump 46 in the anticoagulant line 42. Alternatively, the recycling line 38 may be connected to a second needle 48, as indicated by the dotted line in FIG. 1, instead of being connected to the inlet line 20.

A plasma branch line 52 is connected to the plasma discharge line 30 at a first branching point 50 downstream from the plasma pump 32 and opens into a storage container 54. An erythrocyte branch line 58 is connected to the erythrocyte discharge line 36 at a second branching point 56 and also opens into the storage container 54.

As shown in FIG. 1, the storage container 54 preferably has an inclined lower edge 60. The erythrocyte branch line 58 opens into the storage container 54 above the plasma branch line 52. The advantage of this is that red blood cells (which have a higher specific gravity than blood plasma) can be mixed more easily with the plasma so that little or no separation of the blood into its components occurs in the storage container 54.

A collecting line 64 is connected between the lowermost end 62 of the storage container 54 and the inlet line 20 at a third branching point 66. The third branching point 66 is upstream of the blood pump 22 between the blood pump 22 and the entry point 40.

A first clamp 68 is disposed in the plasma discharge line 30 downstream of the first branching point 50, and a second clamp 70 is disposed in the plasma branch line 52 downstream of the first branching point 50. The clamps 68 and 70 form a first clamp pair.

A third clamp 72 is disposed in the erythrocyte discharge line 36 downstream of the second branching point 56 and a fourth clamp 74 is disposed in the erythrocyte branch line 58 downstream of the second branching point 56. The two clamps 72 and 74 form a second clamp pair.

A fifth clamp 76 is disposed in the collecting line 64 upstream of the third branching point 66 and a sixth clamp 78 is disposed in the inlet line 20 between blood pump 22 and entry point 40. The clamps 76 and 78 form a third clamp pair.

The first, second and third clamp pairs are connected to one another through a clamp control device 80 in such a way that the first, third and fifth clamps 68, 72, 76 are always closed when the second, fourth and sixth clamps 70, 74, 78 are opened, or after the clamp control device 80 switches the positions of the clamps the first, third and fifth clamps 68, 72, 76 are opened when the second, fourth and sixth clamps 70, 74, 78 are closed.

The clamps 68–78 can be closed or opened via the mechanical clamp control device 80; however, an alternative clamp control can be used, such as an electrical control device (not shown), so that the clamps can be operated separately.

A plasma collecting line 84 is connected to the plasma discharge line 30 at a fourth branching point 82 downstream of the first clamp 68 and opens into a plasma collecting bag 86. A seventh clamp 88 is provided in the plasma collecting line 84 downstream of the fourth branching point 82, and an eighth clamp 90 is disposed in the plasma discharge line 30 downstream of the fourth branching point 82. The seventh and eighth clamps 88, 90 form a fourth clamp pair. The opening and closing of the fourth clamp pair is independent of that of the clamps 68–78. When one of the clamps 88, 90 is closed, the other of the clamps 88, 90 is open.

The degree to which the storage container 54 is filled is determined advantageously with a level detector 92, which can be designed as a weight or level sensor and which determines the amount of blood introduced into the storage container 54 according to weight or volume. After the weight or volume of blood inside the storage container 54 reaches a predetermined value, the level detector 92 triggers a switching process. A locking device 94 is provided in the return line 38 in order to be able to switch the arrangement into a safe state.

Figure 2:
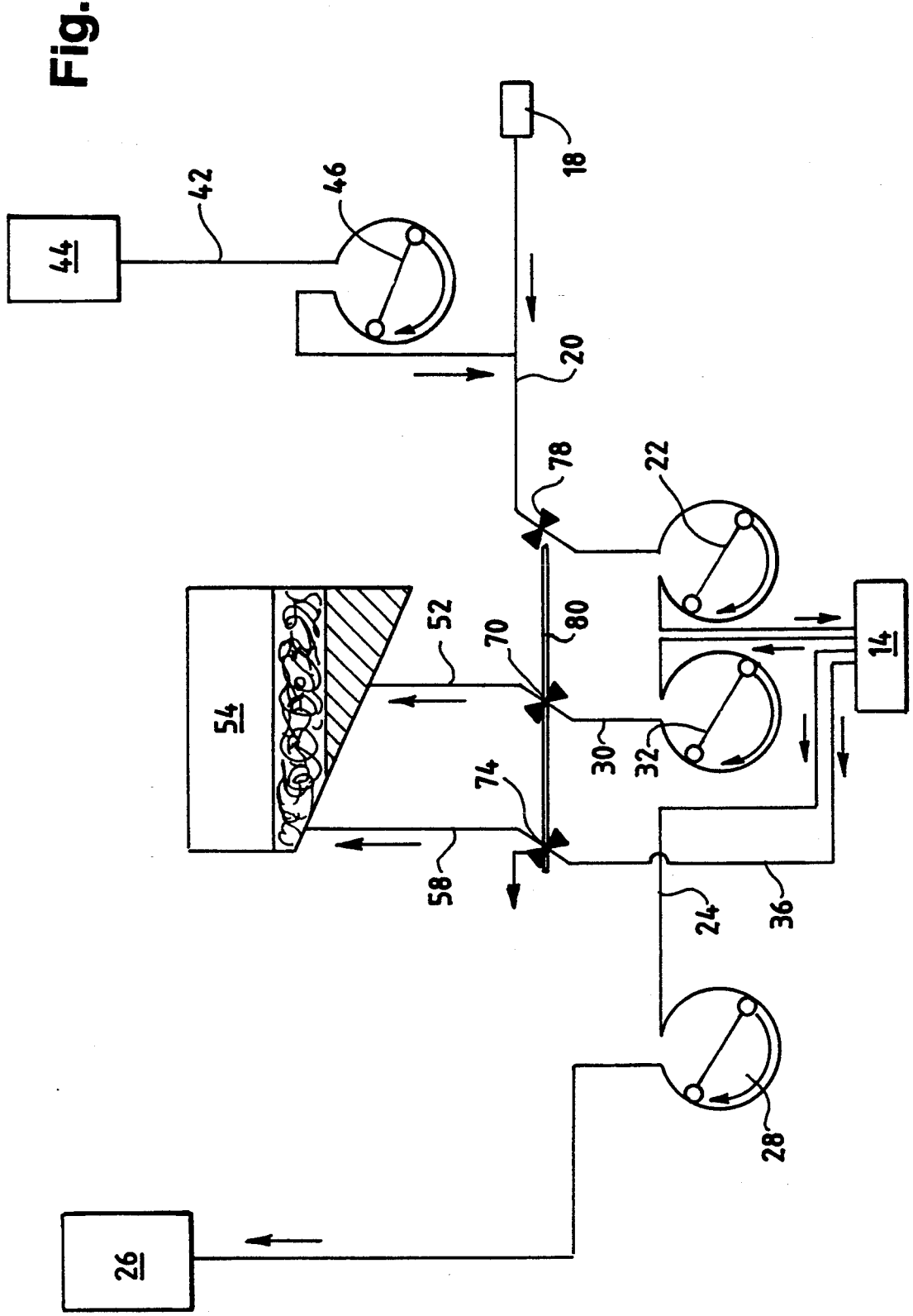
FIG. 2 is the embodiment of FIG. 1 in the collection phase with some components not shown for sake of clarity; and, FIG. 3 is the embodiment of FIG. 1 in the recirculation phase with some components not shown for sake of clarity.

FIG. 2 shows the centrifuge system 10 of FIG. 1 in the collection phase, omitting for purposes of simplicity parts of the system that are not used in the collection phase. In FIG. 2, the clamps 70, 74 and 78 are in the open position, which is illustrated by their being shown completely blackened.

In the collection phase, blood is introduced through the needle 18 and is pumped to the separation chamber 14 via the inlet line 20 by the blood pump 22. With the aid of the anticoagulant pump 46, anticoagulant solution is provided to the inlet line 20 via the line 42 where it mixes with the blood.

According to a known separation method, for example, as described in DE-OS 33 01 113, the blood is separated into its components in the separation chamber 14, and plasma is pumped through the plasma discharge line 30 into the storage container 54 via the plasma pump 32. White blood cells and platelets are transferred through the WBC-PLT discharge line 24 into the WBC-PLT bag 26 with the aid of the WBC-PLT pump 28. Red blood cells present in the separation chamber 14 are transferred to the storage container 54 via the erythrocyte discharge line 36 and are mixed there with the plasma. As soon as a predetermined amount of blood is present in the storage container 54, a switching process is triggered by the detector 92. Alternatively, the switching process can be triggered by the blood pump 22 after it pumps a certain amount of blood.

Figure 3:
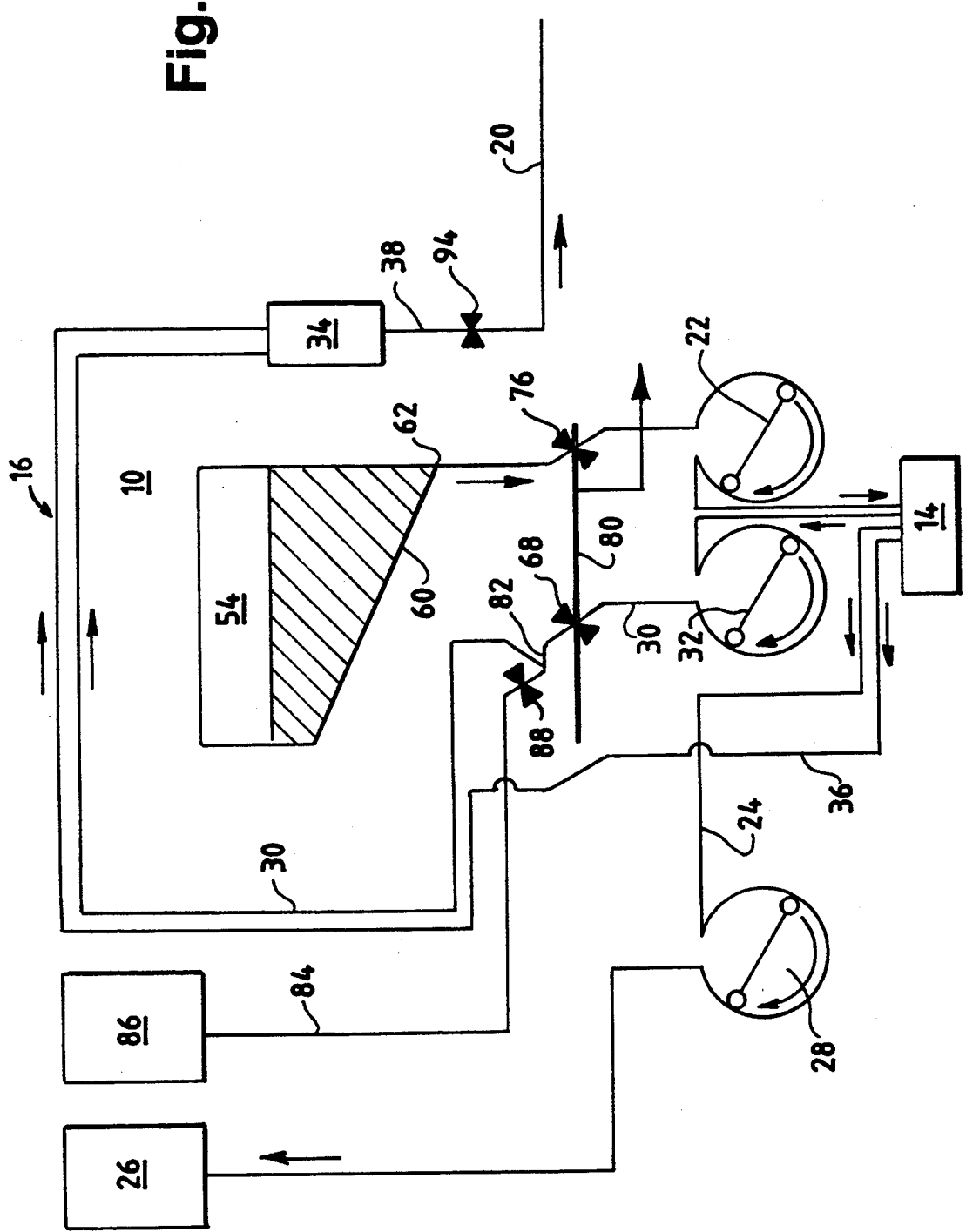

The switching process switches the clamp control 80 from the collection phase, as shown in FIG. 2, into the recirculation phase, as shown in FIG. 3. In FIG. 3, the parts of the system that are not necessary in the recirculation phase or are deactivated in this phase are omitted for the sake of simplicity.

Referring to FIG. 3, in the recirculation phase, the first, third and fifth clamps 68, 72 (FIG. 1), 76 are open, and the blood pump 22 pumps blood from the storage container 54 (instead of from the needle 18) into the separation chamber 14 in order to trigger a second separation process on almost the same blood volume.

After renewed separation of the blood, which can lead to an improvement of the degree of separation of white blood cells of up to 90%, the red blood cells are transferred through the erythrocyte discharge line 36 and the plasma is transferred through the plasma discharge line 30 to the dropping chamber 34 where these two components are mixed intensely. From there, the blood is returned to the needle 18 through the return line 38, the inlet line 20 (which now serves as a return line), and to the patient or the blood bag. During this reinfusion phase, white blood cells and platelets are pumped through the WBC-PLT line 24 into the WBC-PLT bag 26.

Plasma can also be collected during the recirculation phase and stored in the plasma collecting bag 86. For this purpose, the clamps 88, 90 are activated alternatively; that is, one of the clamps 88, 90 is opened and the other is closed. Only sufficient plasma is withdrawn so that recycling of the otherwise too-viscous red blood cells is not hindered.

Usually, the clamp 94 is closed during the collection phase and opened during the reinfusion phase. However, since one should be able to close it at any time (for example, in cases of alarm), the clamp 94 is not connected to a rigid valve drive, such as that provided by the valve control device 80.

After the storage container 54 is empty, which can be detected by the detector 92 or the separation chamber 14 as described in DE-OS 33 01 113 mentioned above, the switching process is triggered again so that the collection phase is started again.

The foregoing detailed description is given for clarity of understanding only, and no unnecessary limitations should be understood therefrom, as modifications within the scope of the invention will be apparent to those skilled in the art.

I claim:

1. A centrifuge system for separating blood into its components, said centrifuge system comprising at least one sampling device for blood, an inlet line connected between the sampling device and a centrifuge and a blood pump disposed in the inlet line, a first discharge line connected between the centrifuge and a first collecting container and a pump disposed in the first discharge line, and a discharge line system for recycling blood components, wherein the discharge line system comprises a plasma discharge line and a pump disposed in the plasma discharge line, a plasma branch line which branches off from the plasma discharge line at a first branching point, the plasma branch line being connected to a storage container, an erythrocyte discharge line and an erythrocyte branch line which branches off from the erythrocyte discharge line at a second branching point, the erythrocyte branch line being connected to the storage container, a collecting line connected between the storage container and the inlet line at a third branching point upstream of the blood pump, and locking means which, in a blood collection cycle, closes the collecting line, the plasma discharge line downstream of the first branching point and the erythrocyte discharge line downstream of the second branching point and opens, in a recirculation cycle, the collecting line, the plasma discharge line downstream of the first branching point and the erythrocyte discharge line downstream of the second branching point and closes in the recirculation cycle, the inlet line upstream of the third branching point, the plasma branch line and the erythrocyte branch line and opens, in the collection cycle, the inlet line upstream of the third branching point, the plasma branch line and the erythrocyte branch line.

2. The centrifuge system of claim 1 wherein the locking means comprises a first clamp disposed in the plasma discharge line downstream of the first branching point and a second clamp disposed in the plasma branch line, a third clamp disposed in the erythrocyte discharge line downstream of the second branching point and a fourth clamp disposed in the erythrocyte branch line, a fifth clamp disposed in the collecting line upstream of the third branching point and a sixth clamp disposed in the inlet line, the first through sixth clamps having either an open position or a closed position, with the positions of the first, third and fifth clamps being controlled to be opposite the positions of the second, fourth and sixth clamps.

3. The centrifuge of claim 2 wherein the first through sixth clamps are operated by a clamp control device.

4. The centrifuge of claim 1 wherein the storage container has an inclined bottom portion and a deepest point and wherein the erythrocyte branch line opens into the storage container at a first entry point, wherein the plasma branch line opens into the storage container at a second entry point, the second entry point being lower than the first entry point, and wherein the collecting line is connected to the storage container at a third entry point, the third entry point being the deepest point of the storage container.

5. The centrifuge system of claim 4 additionally comprising a level sensor for detecting the degree to which the storage container is filled, the level sensor switching the state of the locking means after reaching a predetermined value.

6. The centrifuge system of claim 1 additionally comprising a plasma collecting line connected between a plasma collecting bag and the plasma discharge line at a fourth branching point downstream of the first clamp and clamp means disposed downstream of the fourth branching point, the clamp means alternately opening and closing the plasma discharge line and the plasma collecting line in a predetermined time frequency.

7. The centrifuge of claim 1 additionally comprising a collecting chamber into which the erythrocyte discharge line and the plasma discharge line open and which is connected to the inlet line.

* * * * *